United States Patent
Susa et al.

[11] Patent Number: 6,125,853
[45] Date of Patent: Oct. 3, 2000

[54] FLAVOR GENERATION DEVICE

[75] Inventors: Masayuki Susa; Manabu Takeuchi, both of Tokyo; Takeshi Kobayashi, Hiratsuka; Hiroshi Sasaki, Hiratsuka; Takeshi Bandai, Hiratsuka, all of Japan

[73] Assignee: Japan Tobacco, Inc., Tokyo, Japan

[21] Appl. No.: 09/029,014

[22] PCT Filed: Jun. 11, 1997

[86] PCT No.: PCT/JP97/02005

§ 371 Date: Feb. 17, 1998

§ 102(e) Date: Feb. 17, 1998

[87] PCT Pub. No.: WO97/48295

PCT Pub. Date: Dec. 24, 1997

[30] Foreign Application Priority Data

Jun. 17, 1996 [JP] Japan .................................. 8-155637

[51] Int. Cl.[7] .................................................. A24F 47/00
[52] U.S. Cl. ........................ 131/273; 131/194; 131/347
[58] Field of Search .................................. 131/273, 270, 131/347, 194

[56] References Cited

U.S. PATENT DOCUMENTS

| | | | |
|---|---|---|---|
| 4,941,483 | 7/1990 | Ridings et al. | 131/194 |
| 4,947,875 | 8/1990 | Brooks et al. | 131/330 |
| 5,249,586 | 10/1993 | Morgan et al. | 131/194 |
| 5,666,977 | 9/1997 | Higgins et al. | 131/194 |
| 5,730,158 | 3/1998 | Collins et al. | 131/194 |

FOREIGN PATENT DOCUMENTS

| | | |
|---|---|---|
| 2704218A | 8/1978 | Germany . |
| 53-071049 | 6/1978 | Japan . |
| 53-139048 | 11/1978 | Japan . |
| 2-55048277 | 11/1980 | Japan . |
| 58-066270 | 5/1983 | Japan . |
| 61-093314 | 5/1986 | Japan . |
| 63-282421 | 11/1988 | Japan . |
| 1-060945 | 4/1989 | Japan . |
| 2-124081 | 5/1990 | Japan . |
| 2-124082 | 5/1990 | Japan . |
| 2-5006993 | 2/1993 | Japan . |

*Primary Examiner*—Christopher A. Fiorilla
*Attorney, Agent, or Firm*—Birch, Stewart, Kolasch & Birch, LLP

[57] ABSTRACT

A flavor generation article including a pipe incorporating a heat reservoir and a formed body serving as a flavor generation medium. The pipe is inserted in an insertion hole of a connection plug, and the connection plug is mounted in a mount hole of a socket. The socket has first and second terminals respectively connected to the two terminals of a power supply. The heat reservoir and formed body in the pipe are heated by a coil heater disposed in the connection plug. When the heater maintains a predetermined temperature for a predetermined period of time, a projection of the mount hole is thermally deformed to be retreated. The connection plug is moved from a mount position by the action of the potential-restoration force of a coil spring and projects from a mount hole integrally with the pipe.

18 Claims, 6 Drawing Sheets

FLAVOR GENERATION DEVICE

This application is the national phase under 35 U.S.C. §371 of prior PCT International Application No. PCT/JP 97/02005 which has an International filing date of Jun. 11, 1997 which designated the United States of America, the entire contents of which are hereby incorporated by reference.

BACKGROUND OF THE INVENTION

1. Technical Field

The present invention relates to a flavor generation article and instrument employed for enjoying inhalation of a flavor and simulated smoking and, more particularly, to a flavor generation article and instrument used for generating a flavor as an inhalation target by heating a material and not by combustion.

2. Background Art

A simulated smoking instrument employed for enjoying the flavor and smoke of tobacco without burning tobacco is already known, and various types of simulated smoking instruments have been proposed.

Jpn. Pat. Appln. KOKAI Publication No. 3-232481 discloses a typical concept of a conventional simulated smoking instrument. The instrument of this reference uses, e.g., a rod-like solid material. When the solid material is heated by an electric heating element, an inhalation target, e.g., a flavor, is generated.

In the simulated smoking instrument utilizing such an electric heating element, when power is supplied to the electric heating element, the temperature of the electric heating element is increased to heat the solid material, so that a flavor component is emitted. Since the solid material has a high specific heat, it takes time to heat the material to a temperature at which the material can sufficiently emit the flavor component. For this reason, when the smoker tries to perform simulated smoking with this instrument, a sufficient amount of flavor component is not emitted instantaneously.

Furthermore, in a simulated smoking instrument of this type, if a power supply is incorporated in the instrument, the internal structure is complicated to increase the cost, and the instrument is difficult to repair. When using of an external power supply, if the power supply and the smoking instrument are connected to each other with a cord, the locations where the instrument can be used are limited, and the cord is an obstacle. Inversely, if the instrument is formed such that it is separate from the external power supply when used for smoking, the heated state of the material can only be maintained for about one or two inhalation (puffing) operations.

U.S. Pat. No. 4,945,931 discloses a simulated smoking instrument using a pressurized aerosol container. In the instrument of this reference, the puffing operation of the user swings the vanes to mechanically open the outlet port of the container, and the aerosol is emitted.

In the instrument utilizing such a pressurized flavor gas source, it is difficult to adjust the opening/closing valve such that the flavor gas can be emitted continuously. More specifically, if the opening/closing valve is formed to have a simple structure, all of the pressurized flavor gas may undesirably be emitted within two or three uses.

SUMMARY OF THE INVENTION

The present invention has been made in view of the above problems, and has as an object to provide a simple flavor generation article and instrument which can emit a sufficient amount of flavor component instantaneously when the smoker tries to perform simulated smoking and which can be used for allowing the puffing operation many times.

According to the first aspect of the present invention, there is provided a flavor generation article employed for allowing inhalation of a flavor, comprising:

a casing having an air intake port for taking in air into the casing and a suction port through which a user inhales the flavor, and forming a gas flow path between the air intake port and the suction port;

a flavor generation medium disposed in the casing to be exposed to the gas flow path and containing a flavor component, the flavor generation medium emitting the flavor component upon being heated; and a heat reservoir disposed in the casing to accumulate heat energy and heat the flavor generation medium with the heat energy.

According to the second aspect of the present invention, there is provided a flavor generation article in which the flavor generation medium comprises a formed body of a solid material containing the flavor component and is arranged adjacent to the heat reservoir.

According to the third aspect of the present invention, there is provided a flavor generation article in which the casing has a heat conduction wall made of a heat-resistant heat-conductive material and arranged to surround the heat reservoir, and a heat-insulating wall made of a heat-insulating material, the heat conduction wall being disposed between the air intake port and the heat-insulating wall, and the heat-insulating wall being disposed between the heat conduction wall and the suction port.

According to the fourth aspect of the present invention, there is provided a flavor generation article which further includes heating means, disposed in the casing, for supplying heat energy to the heat reservoir.

According to the fifth aspect of the present invention, there is provided a flavor generation article in which the heating means is an electric heater.

According to the sixth aspect of the present invention, there is provided a flavor generation article which further includes means for supplying electric energy to the electric heater.

According to the seventh aspect of the present invention, there is provided a flavor generation instrument employed for allowing inhalation of a flavor, characterized by comprising:

(a) an external heating mechanism including an insertion hole for accepting and heating an elongated body, and heating means disposed along the insertion hole; and (b) a flavor generation article detachably inserted in the insertion hole of the external heating mechanism, the flavor generation article having an incombustible casing with an air intake port for taking in air into the casing and a suction port through which a user inhales the flavor, and forming a gas flow path between the air intake port and the suction port, a flavor generation medium disposed in the casing to be exposed to the gas flow path and containing a flavor component, the flavor generation medium emitting the flavor component upon being heated, and a heat reservoir disposed in the casing to accumulate heat energy and heat the flavor generation medium with the heat energy, the heat reservoir being arranged to receive the heat energy from the heating means when the flavor generation article is inserted in the insertion hole of the external heating mechanism.

According to the eighth aspect of the present invention, there is provided a flavor generation article in which the flavor generation medium is a formed body of a solid material containing the flavor component and is arranged adjacent to the heat reservoir.

According to the ninth aspect of the present invention, there is provided a flavor generation article in which the heating means is an electric heater.

According to the 10th aspect of the present invention, there is provided a flavor generation article in which the casing has a heat conduction wall made of a heat-resistant heat-conductive material, and is arranged to be heated by the heating means of the connection plug, and a heat-insulating wall made of a heat-insulating material, the heat conduction wall being arranged between the air intake port and the heat-insulating wall, and the heat-insulating wall being arranged between the heat conduction wall and the suction port.

According to the 11th aspect of the present invention, there is provided a flavor generation article further including means for correlating an attaching/detaching operation of the flavor generation article in/from the insertion hole of the external heating mechanism and an on/off operation of the electric heater.

According to the 12th aspect of the present invention, there is provided a flavor generation instrument employed for allowing inhalation of a flavor, comprising:

(a) an external heating mechanism including an insertion hole for accepting and heating an elongated body, and first and second terminals connected to a power supply and arranged in the insertion hole; and (b) a flavor generation article detachably inserted in the insertion hole of the external heating mechanism, the flavor generation article comprising an incombustible casing having an air intake port for taking in air into the casing and a suction port through which a user inhales the flavor, and forming a gas flow path between the air intake port and the suction port, a flavor generation medium disposed in the casing to be exposed to the gas flow path and containing a flavor component, the flavor generation medium emitting the flavor component upon being heated, a heat reservoir disposed in the casing to accumulate heat energy and heat the flavor generation medium with the heat energy, an electric heater disposed in the casing to supply the heat energy to the heat reservoir, and first and second electric contacts exposed outside the casing and serving as circuit terminals of the electric heater, the first and second electric contacts coming into contact with the first and second terminals, respectively, when the flavor generation article is inserted in the insertion hole of the external heating mechanism.

According to the 13th aspect of the present invention, there is provided a flavor generation article in which the flavor generation medium is a formed body of a solid material containing the flavor component and is arranged adjacent to the heat reservoir.

According to the present invention, there is provided a simple flavor generation article and instrument which can emit a sufficient amount of flavor component instantaneously when the smoker tries to perform simulated smoking and which can be used for allowing the puffing operation many times. In particular, if the flavor generation instrument utilizes the cigarette lighter socket of a seat of an automobile or air plane, in a house, or the like, the flavor generation instrument can have a simple structure and can be used for allowing the puffing operation many times without contaminating air in a small space. The socket of the flavor generation instrument can be made portable as far as the power supply can be ensured.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

The embodiments of the present invention will be described below with reference to the accompanying drawings. In the accompanying drawings, it is explicitly stated that the respective elements are now shown to scale in order to facilitate understanding of the contents.

Figure 1:
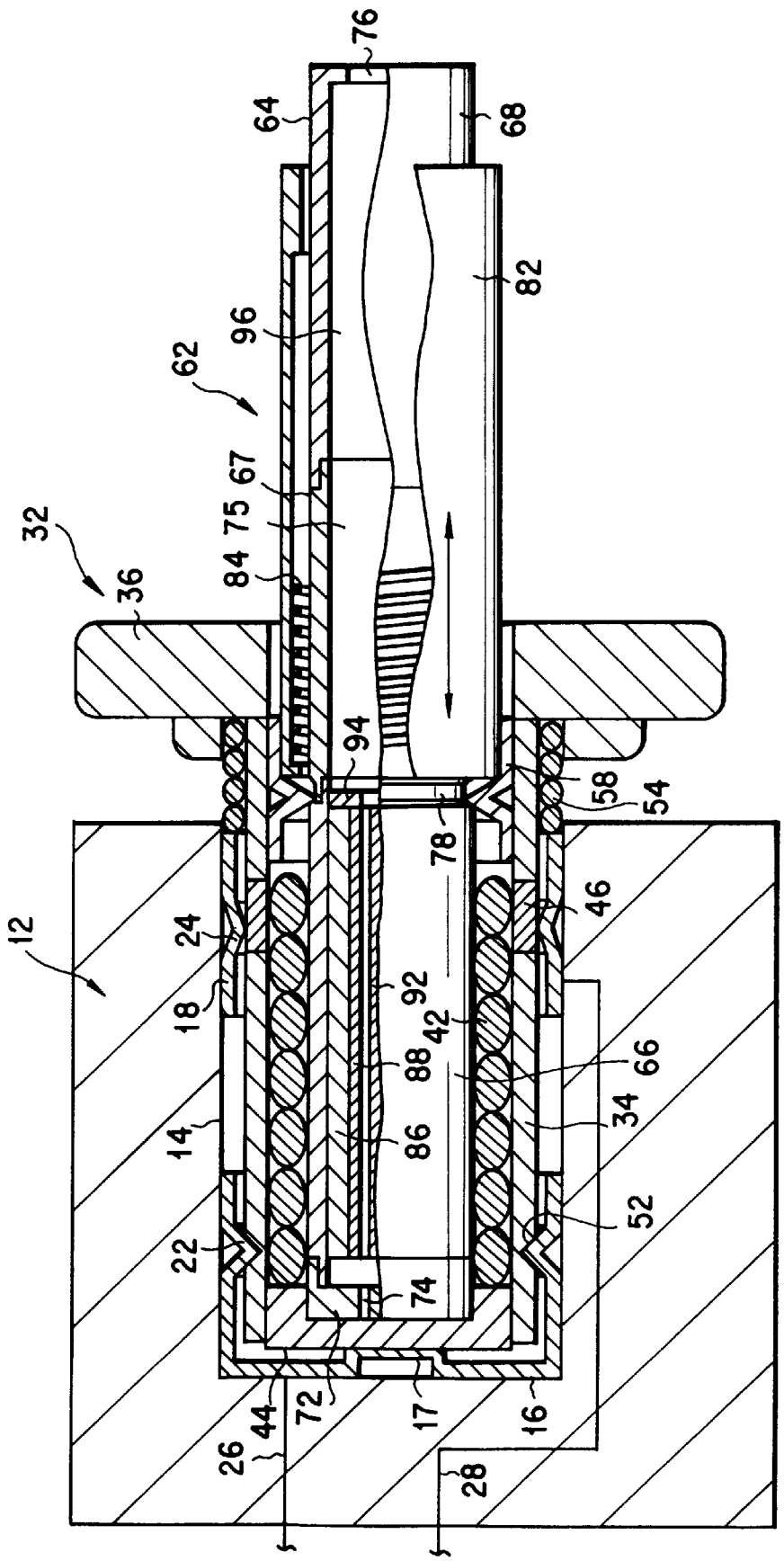
FIG. 1 is a schematic view showing a flavor generation article and instrument according to an embodiment of the present invention.

FIG. 1 is a schematic view showing a flavor generation article and instrument according to an embodiment of the present invention. In this embodiment, the flavor generation article corresponds to a pipe 62 incorporating a formed body 88 as a flavor generation medium and a heat reservoir 86, as will be described later in detail. The flavor generation instrument is constituted by the pipe 62 and an external heating mechanism including a connection plug 32 for heating the pipe 62, and a socket 12. As the socket 12, a cigarette lighter socket 12 typically disposed at the driver's seat of an automobile, or at the seat of an air plane or house depending on the case, can be utilized.

The cigarette lighter socket 12 has a cylindrical mount hole 14 for mounting a cigarette lighter (not shown) therein and supplying power to it. First and second terminals 16 and 18, which are connected to the two terminals of a power supply mounted in the automobile or the like through lines 26 and 28, respectively, are disposed in the mount hole 14.

Annular projections 22 and 24 projecting in the radial direction are respectively formed on the terminals 16 and 18 to lock the cigarette lighter.

The first terminal 16 forms a hollow cylinder having a bottom portion, and is fixed to be seated on the bottom portion of the mount hole 14. A contact projection 17 is formed on the bottom wall of the first terminal 16. The side wall of the first terminal 16 extends along the inner side surface of the mount hole 14 in an unfixed state, and the annular projection 22 is formed on part of it. The second terminal 18 forms a hollow cylinder having two open end faces, and is fixed near the inlet port of the mount hole 14 through its one end portion. The free end portion side of the second terminal 16 extends along the inner side surface of the mount hole 14 in an unfixed state toward the bottom portion of the mount hole 14, and the annular projection 24 is formed on part of it.

The projections 22 and 24 are formed by bending portions of the side walls of the cylindrical terminals 16 and 18 inwardly. The terminal 16 is made of a thermally deformable known bimetal. When it is heated, the terminal 16 is stretched in the axial direction of the cylindrical shape. Therefore, when the terminal 16 is heated, the projection 22 is retreated by thermal deformation toward the inner side surface of the mount hole 14.

The connection plug 32 is mounted in the mount hole 14 of the cigarette lighter socket 12. As shown in the enlarged view of FIG. 2, the connection plug 32 has a frame 34 which is detachably inserted in the mount hole 14 of the cigarette lighter socket 12. The frame 34 forms a hollow cylinder having two open end faces in order to form an insertion hole 38 for accepting the pipe 62. At the inlet port-side end portion of the insertion hole 38, a flange 36 is formed on the frame 34.

A coil heater 42 is disposed inside the frame 34 so as to substantially define the inner side surface of the insertion hole 38. The coil heater 42 is connected to first and second electric contacts 44 and 46 serving as its circuit terminals. The first electric contact 44 forms the bottom portion of the insertion hole 38 and is exposed outside the connection plug 32 through the opening of the frame 34. The second electric contact 46 extends through the side wall of the frame 34 to be exposed outside the connection plug 32.

An engaging portion, i.e., an annular groove 52, is formed in the outer side surface of the frame 34 so as to engage with the annular projection 22 formed by the first terminal 16 in the mount hole 14. When the connection plug 32 is located at the mount position in the mount hole 14 of the cigarette lighter socket 12, the projection 22 enters the groove 52 to lock the connection plug 32. At this time, the first electric contact 44 comes into contact with the projection 17 of the first terminal 16, and the second electric contact 46 comes into contact with the projection 24, constituted by the second terminal 18, while squeezing the projection 24.

A coil spring 54 is disposed to wind around the frame 34 near the flange 36. One end portion of the coil spring 54 is fixed in a groove 56 formed between the annular projection of the flange 36 and the frame. When the connection plug 32 is locked at the mount position in the mount hole 14, the coil spring 54 is compressed between the casing wall surface, that surrounds the inlet port of the mount hole 14, and the flange 36. Hence, a potential-restoration force for moving the connection plug 32 from the mount position in the mount hole 14 to disconnect the first and second terminals 16 and 18 from the first and second electric contacts 44 and 46, respectively, is given to the connection plug 32.

An annular projection 58 for locking the pipe 62 is also disposed in the insertion hole 38 of the connection plug 32. The annular projection 58 is formed by bending part of a cylindrical ring, and can elastically lock the pipe 62.

The pipe 62 has a cylindrical casing 64 having such an outer diameter that the user can hold the casing 64 in his mouth. The casing 64 has a heat conduction tube 66 and a heat conduction cap 72 each made of a heat-resistant heat-conductive material, e.g., a metal or a ceramic, and a heat-insulating tube 67 and a mouthpiece 68 each made of a heat-resistant heat-insulating material, e.g., a synthetic resin. These members 66, 67, 68, and 72 are detachably connected to each other with known connection structures, e.g., screws or fitting pairs. Depending on the temperature employed, the casing 64 can be made of various types of materials. As the material of the casing 64, for example, paper or pulp can be used if the employed temperature is equal to or lower than 200° C., a heat-resistant plastic is used if the employed temperature is between 200° C. and 400° C., and a ceramic or metal can be used if the employed temperature is equal to or higher than 400° C.

A plurality of air intake ports 74 for taking in air into the casing 64 are formed in the cap 72. In contrast to this, a suction port 76 through which the user inhales the flavor is formed in the end portion of the mouthpiece 68. A gas flow path 75 is defined in the casing 64 between the air intake ports 74 and the suction port 76.

An annular groove 78, the two surfaces of which are tapered, is formed in the outer side surface of the casing 64 to correspond to the connecting portion of the heat conduction tube 66 and heat-insulating tube 67. When the pipe 62 is located at the insertion position in the insertion hole 38 of the connection plug 32, the projection 58 enters the annular groove 78 to lock the pipe 62.

A cover 82 made of a heat-resistant heat-insulating material, e.g., a synthetic resin, is slidably mounted on the casing 64. A coil spring 84 is disposed in the cover 82. When no load is applied, the cover 82 covers the heat conduction tube 66 and cap 72. However, when the pipe 62 is to be locked at the insertion position in the insertion hole 38, the cover 82 is pushed out by the projection 58 against the biasing force of the coil spring 84 to a position where it covers the heat-insulating tube 67. More specifically, in the insertion hole 38, the heat conduction tube 66 directly opposes the coil heater 42.

A laminated heat reservoir 86 is disposed in the heat conduction tube 66 to cover the entire inner surface of the heat conduction tube 66, and the formed body 88 of the solid material serving as the flavor generation medium for generating flavor or the like to be inhaled by the user is detachably stored inside the heat reservoir 86. The formed body 88 is positioned as it abuts against a projection 94 formed on the inner surface of the heat conduction tube 66. The heat reservoir 86 is used to maintain the temperature of the formed body 88 at the flavor generation temperature for a longer period of time.

The formed body 88 is formed as a dense cylinder having a low air permeability, and has such a size that no gap is formed between its outer surface and the inner surface of the heat reservoir 86. Accordingly, a plurality of through holes 92 are formed in the formed body 88 in the axial direction, and the gas flow path 75 between the air intake ports 74 and suction port 76 is formed through the through holes 92.

As the material of the heat reservoir 86, a sensible heat type material utilizing only the specific heat capacity of a substance, e.g., an inorganic compound such as silica gel, alumina, carbons, glass mat, glass fiber, or minerals; a metal or an alloy such as aluminum, iron, silver, or lead; a cellulose material such as paper or pulp; paper added with an inorganic substance or carbon; or metal-laminated paper can be used. As another heat accumulating material, a material utilizing heat of fusion in order to increase the quantity of heat, e.g., a compound such as paraffin, sodium acetate, naphthalene, wax, or polyethylene oxide, or a metal or an alloy, such as zinc, tin, or solder (soft wax), may be filled in a closed container made of a high heat conductivity. More specifically, when generating aerosol, it is preferable to use a sensible heat type material or a material having a melting point of 200° C. to 300° C. and utilizing heat of fusion; and when generating only flavor, it is preferable to use a material having a melting point of 50° C. to 200° C. and utilizing heat of fusion.

The formed body 88 of the material serving as the medium that generates a flavor not by combustion but by heating can contain an extracted material and/or its constituent components of various types of natural materials in accordance with the application purpose. As the flavor substance to be contained by the flavor generation medium, for example, menthol, caffeine, a precursor, e.g., glycoside, that generates flavor upon thermal decomposition, or a tobacco component, e.g., a tobacco extract component or a tobacco smoke condensate component can be employed. In order to add smoke to the flavor, the flavor generation medium can contain a material which generates aerosol when heated. As the material that generates aerosol, polyols, e.g., glycerin or propylene glycol, lower alcohols, saccharides, or their mixtures can be used. The flavor generation medium can contain a gas adsorbent, e.g., activated carbon, silica gel, or activated alumina.

The formed body 88 serving as the flavor generation medium can be formed to such a size that a gap is formed between its outer surface and the inner surface of the heat reservoir 86. The formed body 88 need not be a dense material having no air permeability but can be a material having a high permeability, e.g., an nonwoven fabric bundle or a fiber bundle made of activated carbon fibers, natural cellulose fibers, or cellulose derivative fibers. In such a case, no through holes 92 need be formed.

The interior of the heat-insulating tube 67 and mouthpiece 68 serves as a cooling chamber 96 constituting part of the gas flow path 75. A filler can be disposed in the cooling chamber 96, in particular in the heat-insulating tube 67. When the filler is disposed, the cooling effect of the gasified flavor component can be promoted, and the pressure loss can be adjusted so that the flavor component can be inhaled with an appropriate pressure. As the filler, for example, a fiber formed body made of cellulose acetate or pulp, or a particulate matter, e.g., glass or aluminum particles, can be used. An outer air inlet hole can be formed in the side wall of the heat-insulating tube 67. In this case, the heated gas containing the flavor generated by the formed body 88 is mixed with the outer air and is cooled in the cooling chamber 96.

Furthermore, a filter can be disposed in the cooling chamber 96, in particular in the mouthpiece 68, to cover the suction port 76. When the filter is disposed, the pressure loss can be adjusted so that the flavor component can be inhaled with an appropriate pressure. The filter can be made of a general tobacco filter material made of cellulose acetate, pulp, or the like. The filter can contain a gas adsorbent, e.g., activated carbon, silica gel, or activated alumina.

The operation of the flavor generation instrument shown in FIG. 1 will be described.

First, the connection plug 32 is mounted in the mount hole 14 of the cigarette lighter socket 12, and the pipe 62 is inserted in the insertion hole 38 of the connection plug 32, to realize the state shown in FIG. 1. In this state, the projection 22 of the mount hole 14 enters the groove 52 of the connection plug 32 to lock the connection plug 32 at the mount position. The coil spring 54 is compressed between the wall surface of the casing surrounding the inlet port of the mount hole 14 and the flange 36. The projection 58 of the insertion hole 38 enters the groove 78 of the pipe 62 to lock the pipe 62 at the insertion position. The cover 82 is pushed outside the insertion hole 38 by the projection 58, and the heat conduction tube 66 directly opposes the heater 42.

When the connection plug 32 is placed at the mount position, the first and second terminals 16 and 18 in the mount hole 14 come into contact with the first and second electric contacts 44 and 46, respectively, of the connection plug 32. Therefore, power is supplied to the coil heater 42 of the connection plug 32, and the heat reservoir 86 and formed body 88 in the pipe 62 are heated by the heater 42 through the heat conduction tube 66 and cap 72. When the heater 42 is maintained at a predetermined temperature for a predetermined period of time, the projection 22, which is made of a bimetal, in the mount hole 14 is thermally deformed, and is retreated from the groove 52 of the connection plug 32 to disengage from it. Therefore, because of the action of the potential-restoration force of the coil spring 54, the connection plug 32 moves from the mount position and slightly projects from the mount hole 14 integrally with the pipe 62.

Thus, the first and second terminals 16 and 18 are disconnected from the first and second electric contacts 44 and 46, respectively, and power supply to the coil heater 42 is interrupted accordingly. Since the connection plug 32 projects from the mount hole 14 integrally with the pipe 62, the user senses this audibly or visually, thus knowing that heating of the pipe 62 is ended.

Subsequently, the pipe 62 is extracted from the connection plug 32, and the pipe 62 is subjected to inhalation of the flavor or simulated smoking. When the pipe 62 is extracted from the connection plug 32, the cover 82 automatically moves to the heat conduction tube 66 side because of the action of the coil spring 84, to cover the heat conduction tube 66 and cap 72. As a result, the pipe 62 can be used in a safe state. The formed body 88 is maintained at a flavor generation temperature for a long period of time because of the action of the heat reservoir 86. Therefore, the pipe 62 can allow inhalation with a puffing operation many times. The formed body 88 of the material after use can be exchanged by removing the cap 72.

Figure 2:
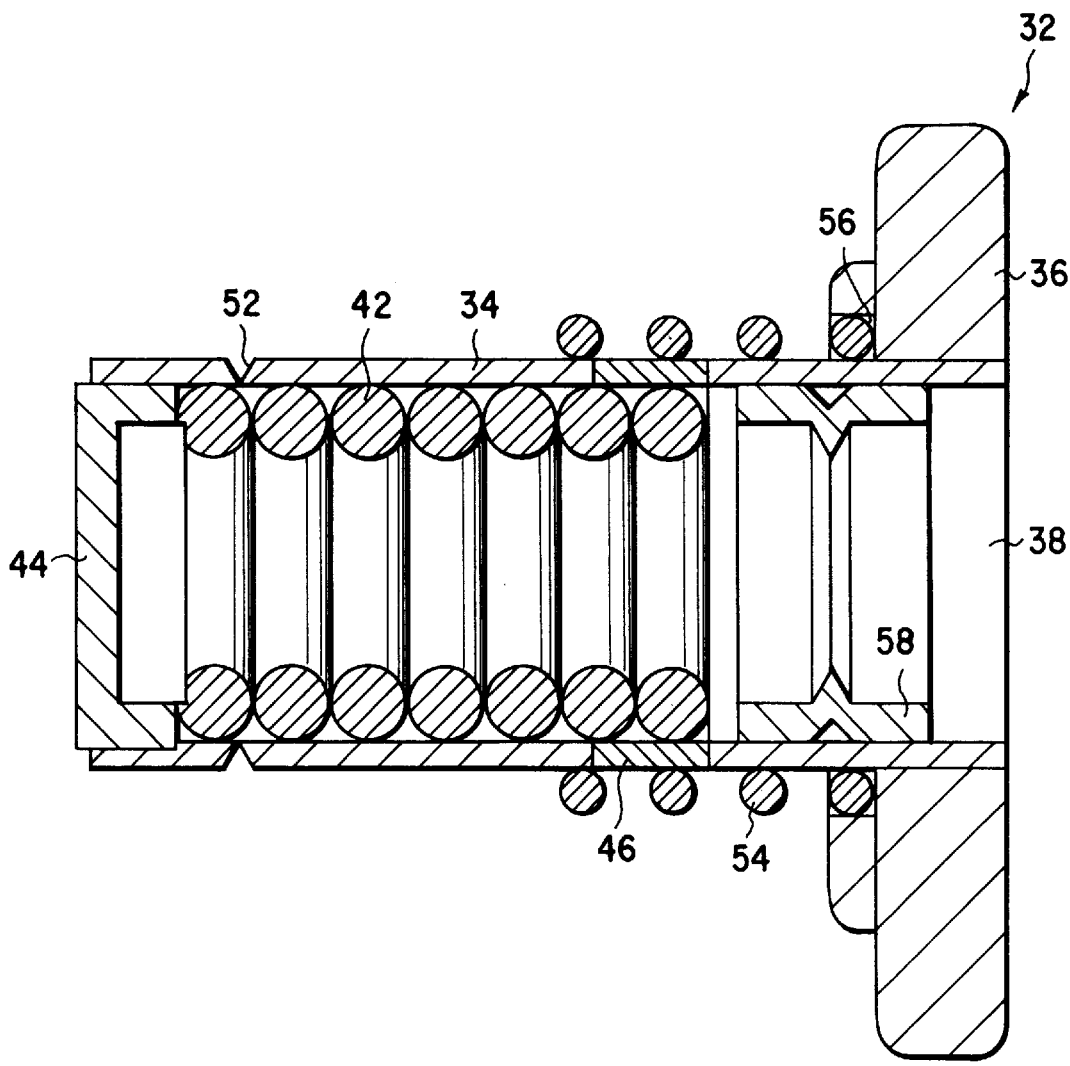
FIG. 2 is an enlarged view showing the connection plug of the flavor generation instrument shown in FIG. 1.
Figure 3:
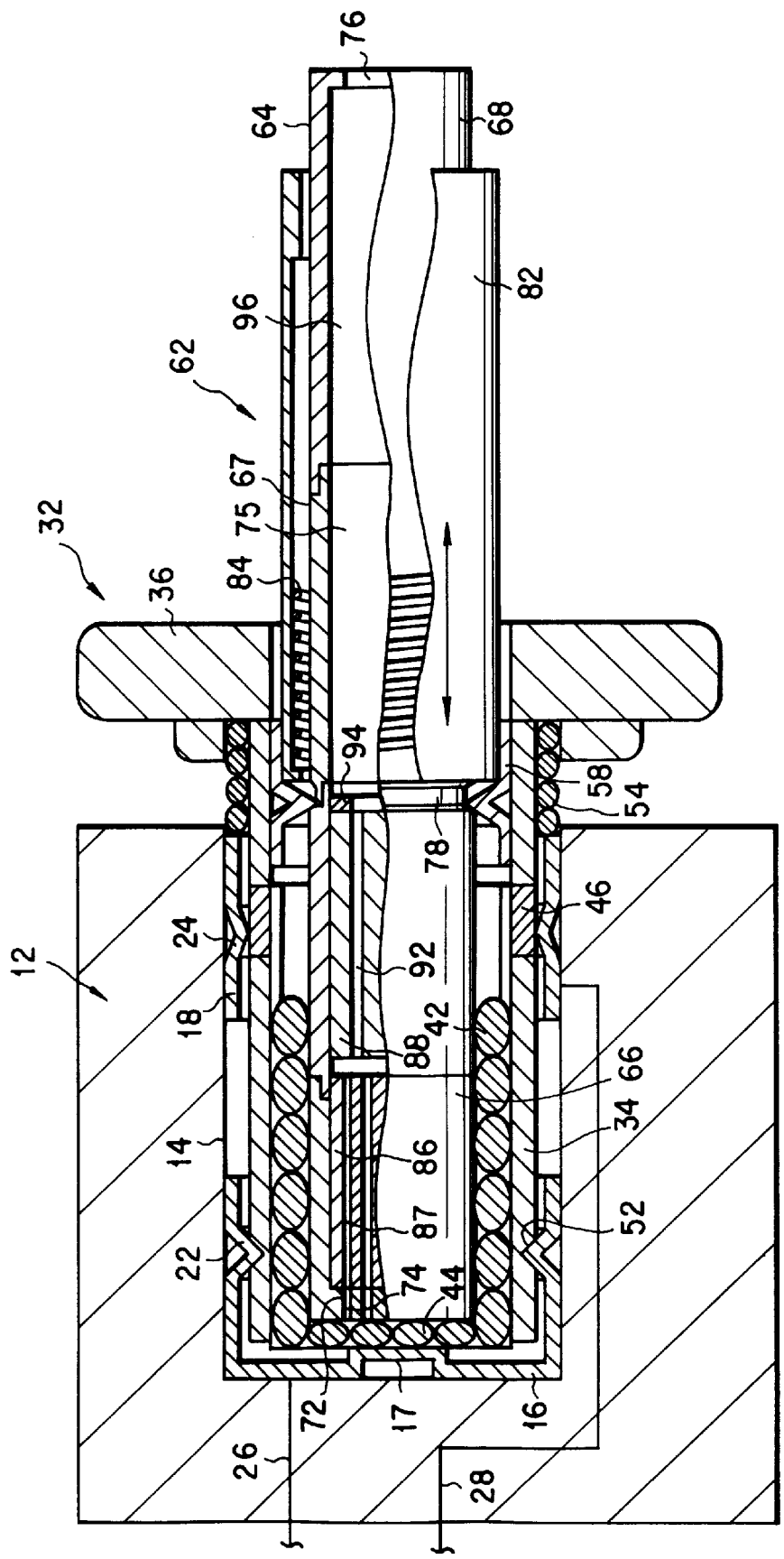
FIG. 3 is a schematic view showing a flavor generation article and instrument according to another embodiment of the present invention.

FIG. 3 is a schematic view showing a flavor generation article and instrument according to another embodiment of the present invention. The arrangement of this embodiment is similar to that of the embodiment shown in FIG. 1. Accordingly, portions of FIG. 3 that are common to FIGS. 1 and 2 are denoted by the same reference numerals as in FIGS. 1 and 2, and a detailed description thereof will be omitted.

In the embodiment shown in FIG. 3, both a heat reservoir 86 and a formed body 88 of the material form cylinders, and are arranged in series at a small gap between them along the longitudinal direction of a casing 64. The heat reservoir 86 is fixed in a heat conduction cap 72 and can be removed together with it. A plurality of through holes 87 are formed in the heat reservoir 86 along the axial direction to be aligned with air intake ports 74. The through holes 87 of the heat reservoir 86 and through holes 92 of the formed body 88 are arranged to be slightly shifted from each other. A coil heater 42 is arranged mainly to be closer to the heat conduction cap 72 and can heat the end face of the cap 72 as well.

The operation of the flavor generation instrument shown in FIG. 3 is basically the same as that of the flavor generation instrument shown in FIG. 1. This will be summarized. First, in the state shown in FIG. 3, the heat reservoir 86 and formed body 88 in a pipe 62 are heated by the coil heater 42, disposed in a connection plug 32, through a heat conduction tube 66 and the cap 72. When the heater 42 maintains a predetermined temperature for a predetermined period of time, a projection 22 of a mount hole 14 is thermally deformed to be retreated. The connection plug 32 is moved from the mount position by the action of the potential-restoration force of a coil spring 54 and slightly projects from the mount hole 14 integrally with the pipe 62. Subsequently, the pipe 62 is extracted from the connection plug 32, so that it can be subjected to inhalation of the flavor or simulated smoking.

Figure 4:
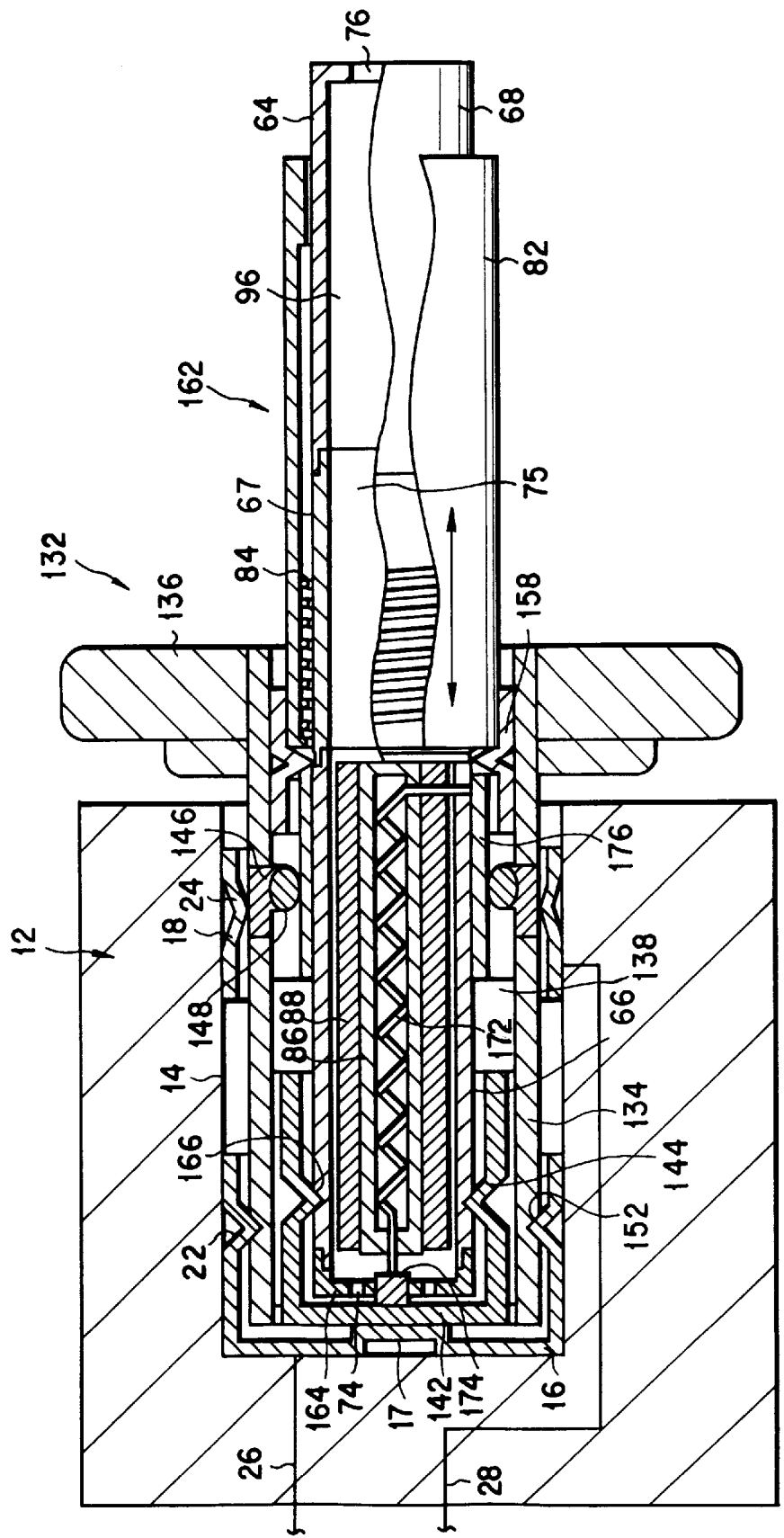
FIG. 4 is a schematic view showing a flavor generation article and instrument according to still another embodiment of the present invention.

FIG. 4 is a schematic view showing a flavor generation article and instrument according to still another embodiment of the present invention. This embodiment is different from the embodiment shown in FIG. 1 in many respects, e.g., in a connection plug 132 and a pipe 162. However, in FIG. 4, portions that are common to FIGS. 1 and 2 are denoted by the same reference numerals as in FIGS. 1 and 2.

In this embodiment, the flavor generation article corresponds to the pipe 162 incorporating a formed body 88, a heat reservoir 86, an electric heater 172, and the like. The flavor generation instrument is constituted by the pipe 162 and an external power supply mechanism including the connection plug 132, which supplies a voltage to the pipe 162, and a socket 12. As described above, as the socket 12, a conventionally used cigarette lighter socket 12 can be used.

The connection plug 132 has a frame 134 which is detachably inserted in a mount hole 14 of the cigarette lighter socket 12. The frame 134 forms a hollow cylinder having two open end faces in order to form an insertion hole 138 for accepting the pipe 162. At the inlet port side end portion of the insertion hole 138, a flange 136 is formed on the frame 134.

The connection plug 132 has first and second electrodes 142 and 146 supported by the frame 134. The first electrode 142 forms a hollow cylinder having a bottom portion and is fixed to the end portion of the frame 134. The first electrode 142 forms the bottom portion of the insertion hole 138 and is exposed outside the connection plug 132 from the opening of the frame 134. The second electrode 146 is annular and is fixed to partially extend through the side wall of the frame 134. The second electrode 146 is exposed outside the connection plug 132 and has an electrode pad 148 projecting into the insertion hole 138.

The side wall of the first electrode 142 extends along the inner side surface of the insertion hole 138 in an unfixed state, and an annular projection 144 is formed on part of it. The projection 144 is formed by bending part of the side wall of the cylindrical first electrode 142 inwardly. The first electrode 142 is made of a thermally deformable known bimetal. When it is heated, the first electrode 142 is stretched in the axial direction of the cylindrical shape. Therefore, when the first electrode 142 is heated, the projection 144 is retreated by thermal deformation toward the inner side surface of the insertion hole 138.

An engaging portion, i.e., an annular groove 152, is formed in the outer side surface of the frame 134 so as to engage with a projection 22 formed by a first terminal 16 in the mount hole 14. When the connection plug 132 is located at the mount position in the mount hole 14 of the cigarette lighter socket 12, the projection 22 enters the groove 152 to lock the connection plug 132. At this time, the first electrode 142 comes into contact with a projection 17 of the first terminal 16, and the second electrode 146 comes into contact with the projection 24, constituted by a second terminal 18, while squeezing the projection 24.

A projection 158 for positioning the pipe 162 and pushing out a cover 82 is also disposed in the insertion hole 138 of the connection plug 132. The projection 158 is formed by bending part of a cylindrical ring, and can elastically position the pipe 162.

The pipe 162 has a cylindrical casing 64 having such an outer diameter that the user can hold the casing 64 in his mouth. The casing 64 has a heat conduction tube 66 made of a heat-resistant heat-conductive material, e.g., a metal or a ceramic, a heat-insulating tube 67 and a mouthpiece 68 each made of a heat-resistant heat-insulating material, e.g., a synthetic resin, and a cap 164 made of a heat-resistant electric-insulating material, e.g., a synthetic resin. These members 66, 67, 68, and 164 are detachably connected to each other with known connection structures, e.g., screws or fitting pairs.

A plurality of air intake ports 74 for taking in air into the casing 64 are formed in the cap 164. In contrast to this, a suction port 76 through which the user inhales the flavor is formed in the end portion of the mouthpiece 68. A gas flow path 75 is defined in the casing 64 between the air intake ports 74 and the suction port 76.

The coil heater 172 is disposed at the center of the heat conduction tube 66 in the axial direction. The coil heater 172 is connected to first and second electric contacts 174 and 176 serving as its circuit terminals. The first electric contact 174 forms a circular disk and is exposed outside the pipe 162 at the center of the end face of the cap 164. The first electric contact 174 is fixed to the cap 164, and is disconnected from the heater 172 when removing the cap 164. The second electric contact 176 forms a cylinder and is fitted and fixed in the outer side surface of the heat conduction tube 66.

The hollow cylindrical heat reservoir 86 is disposed to cover the coil heater 172, and the formed body 88 of the solid material for generating flavor or the like to be inhaled by the user is detachably mounted on the heat reservoir 86. The formed body 88 has such a size that a gap is formed between it and the inner surface of the heat conduction tube 66. Accordingly, the gas flow path 75 between the air intake ports 74 and suction port 76 is formed through this gap. As the materials of the heat reservoir 86 and formed body 88, those that are mentioned in connection of the flavor generation instrument shown in FIG. 1 can be used.

An annular groove 166 is formed in the outer side surface of the heat conduction tube 66. When the pipe 162 is located at the insertion position in the insertion hole 138 of the connection plug 132, the projection 144 of the first electrode 142 enters the groove 166 to lock the pipe 162. At this time, the first electric contact 174 comes into contact with the first electrode 144, and the second electric contact 176 comes into contact with the electrode pad 148 of the second electrode 146.

The cover 82 made of a heat-resistant heat-insulating material, e.g., a synthetic resin, is slidably mounted on the casing 64. A coil spring 84 is disposed in the cover 82. When no load is applied, the cover 82 covers the heat conduction tube 66. However, when the pipe 162 is locked at the insertion position in the insertion hole 138, the cover 82 is pushed out by the projection 158 against the biasing force of the coil spring 84 to the position where it covers the heat-insulating tube 67. Hence, a potential-restoration force for moving the pipe 162 from the insertion position in the insertion hole 138 to disconnect the first and second electrodes 142 and 146 from the first and second electric contacts 174 and 176, respectively, is given to the pipe 162.

The operation of the flavor generation instrument shown in FIG. 4 will be described.

First, the connection plug 132 is mounted in the mount hole 14 of the cigarette lighter socket 12, and the pipe 162 is inserted in the insertion hole 138 of the connection plug 132, to realize the state shown in FIG. 4. In this state, the projection 22 of the mount hole 14 enters the groove 152 of the connection plug 32 to lock the connection plug 132 at the mount position. The projection 144 of the insertion hole 138 enters the groove 166 of the pipe 162 to lock the pipe 162 at the insertion position. The cover 82 is pushed outside the insertion hole 138 by the projection 158, and the coil spring 84 is compressed in the cover 82.

When the connection plug 132 and pipe 162 are placed at the mount and insertion positions, respectively, the first and second terminals 16 and 18 in the mount hole 14 are connected to the first and second electric contacts 174 and 176 of the pipe 162 through the first and second electrodes 142 and 146 of the connection plug 132, respectively. Power is supplied to the coil heater 172 of the pipe 162, and the heat reservoir 86 and formed body 88 are heated by the heater 172. When the heater 172 maintains a predetermined temperature for a predetermined period of time, the projection 144, which is made of a bimetal, in the insertion hole 138 is thermally deformed, to be retreated to disengage from the groove 166 of the pipe 162. Therefore, because of the action of the potential-restoration force of the coil spring 84, the pipe 162 moves from the insertion position to project from the insertion hole 138 leaving the connection plug 132 behind.

The first and second electrodes 142 and 146 are then disconnected from the first and second electric contacts 174 and 176, respectively, and power supply to the coil heater 172 is interrupted. Since the pipe 162 projects from the insertion hole 138, the user senses this audibly or visually, thus knowing that heating of the pipe 162 is ended.

Subsequently, the pipe 162 is disconnected from the connection plug 132, and the pipe 162 is subjected to inhalation of the flavor or simulated smoking. The cover 82 automatically moves to the heat conduction tube 66 side because of the action of the coil spring 84, to cover the heat conduction tube 66. As a result, the pipe 162 can be used in a safe state. The formed body 88 is maintained at a flavor generation temperature for a long period of time because of the action of the heat reservoir 86. Therefore, the pipe 162 can allow inhalation with a puffing operation many times. The formed body 188 of the material after use can be exchanged by removing the cap 164.

In the flavor generation instrument shown in FIG. 4, the heat conduction tube 66 is made of a material having a high heat conductivity in order to thermally actuate the projection 144 made of a bimetal. However, if the thermal sensitivity of the projection 144 is improved, the tube 66 can be made of a material, the heat conductivity of which is not so high. If the connection plug 132 itself is disposed with a means for causing the projection 144 to retreat under a predetermined condition, e.g., a combined structure of a heater and a timer, the tube 66 can be made of a heat-insulating material. When the pipe 162 is to be manually pulled out from the connection plug 132 as well, the tube 66 can be made of a heat-insulating material. In this case, the cover 82 incorporating the coil spring 84 becomes unnecessary.

Figure 5:
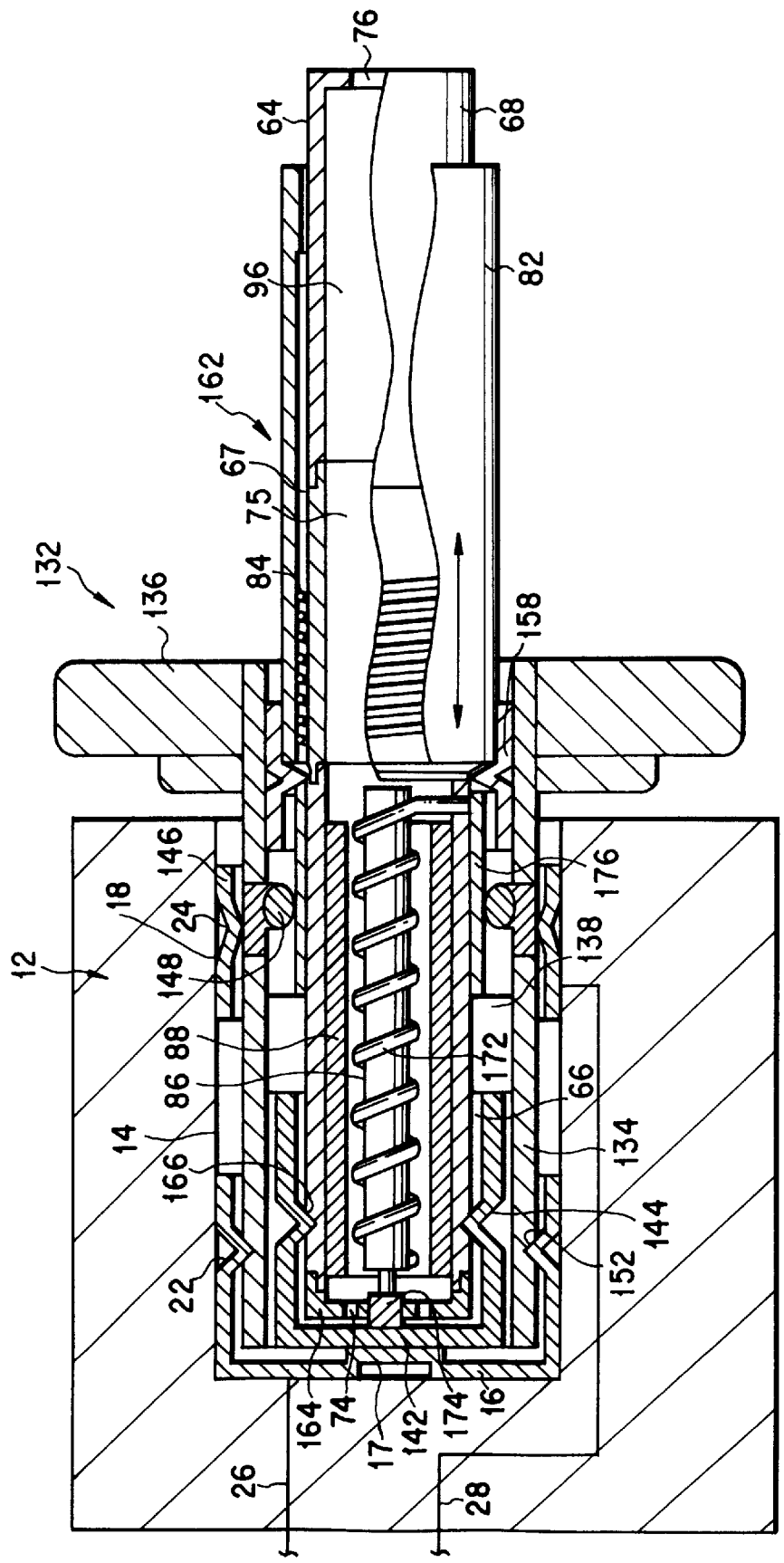
FIG. 5 is a schematic view showing a flavor generation article and instrument according to still another embodiment of the present invention.

FIG. 5 is a schematic view showing a flavor generation article and instrument according to still another embodiment of the present invention. The arrangement of this embodiment is similar to that of the embodiment shown in FIG. 4. Accordingly, in FIG. 5, portions that are common to FIG. 4 are denoted by the same reference numerals as in FIG. 4, and a detailed description thereof will be omitted.

In the embodiment shown in FIG. 5, a coil heater 172 is disposed to wind around an elongated heat reservoir 86, and a formed body 88 of the material forms a hollow cylinder to surround the coil heater 172. The formed body 88 is formed to such a size that no gap is formed between it and the inner surface of a heat conduction tube 66. Accordingly, a gas flow path 75 between air intake ports 74 and a suction port 76 is formed through a central through hole of the formed body 88.

The operation of the flavor generation instrument shown in FIG. 5 is basically the same as that of the flavor generation instrument shown in FIG. 4. This will be summarized. First, in the state shown in FIG. 5, the heat reservoir 86 and formed body 88 in a pipe 162 are heated by the coil heater 172. When the heater 172 maintains a predetermined temperature for a predetermined period of time, a projection 144 of an insertion hole 138 is thermally deformed to be retreated. The pipe 162 is moved from the insertion position by the action of the potential-restoration force of a coil spring 84 and projects from the insertion hole 138. Subsequently, the pipe 162 is disconnected from a connection plug 132, so that it can be subjected to inhalation of the flavor or simulated smoking.

Figure 6:
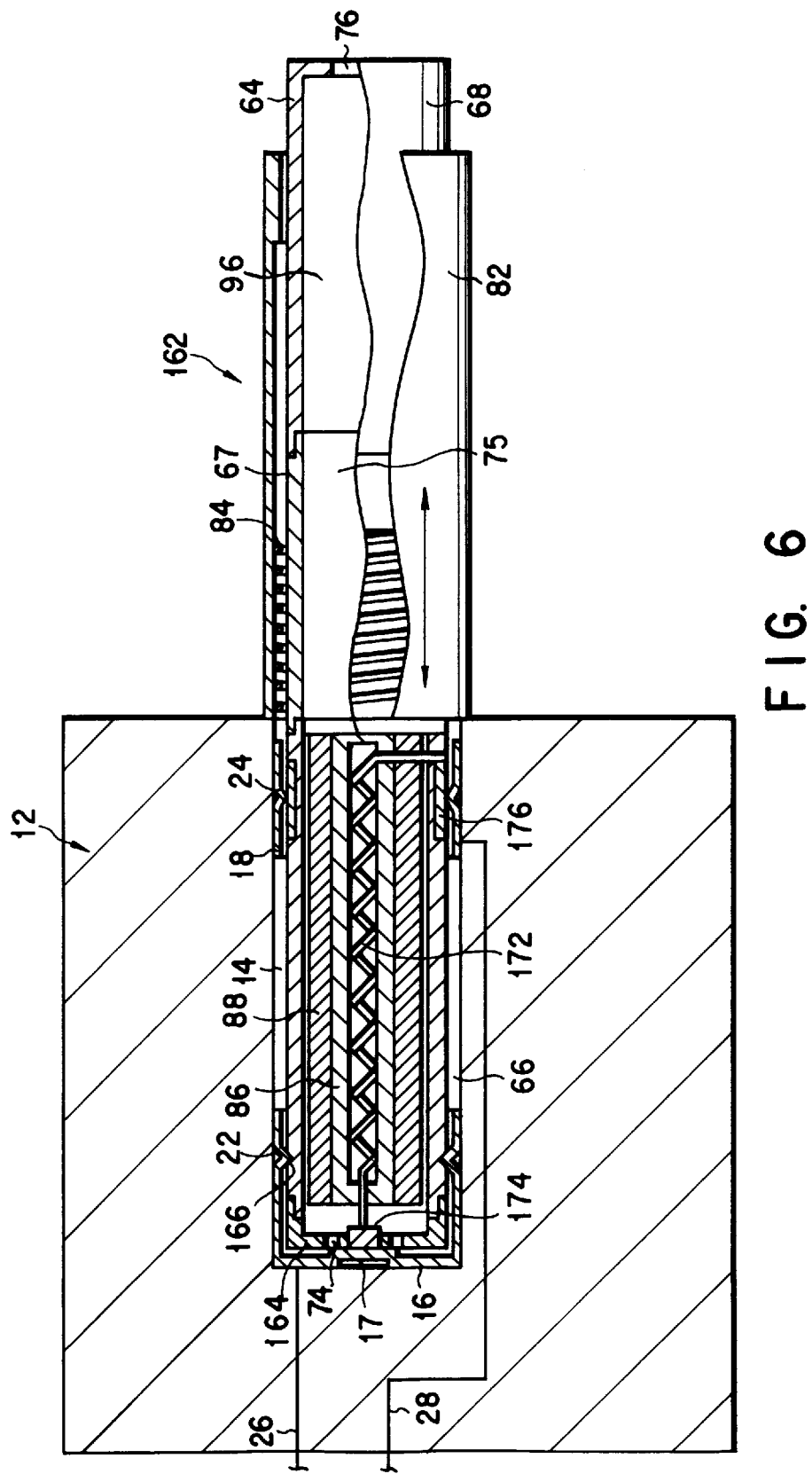
FIG. 6 is a schematic view showing a flavor generation article and instrument according to still another embodiment of the present invention.

FIG. 6 is a schematic view showing a flavor generation article and instrument according to still another embodiment of the present invention. The characteristic feature of the flavor generation instrument of this embodiment resides in that it does not use a connection plug 132 but a pipe 162 is directly mounted on a socket 12, e.g., a cigarette lighter socket 12. However, the pipe 162 itself is substantially the same as that shown in FIG. 4. Accordingly, in FIG. 6, portions that are common to FIG. 4 are denoted by the same reference numerals as in FIG. 4, and a detailed description thereof will be omitted.

In the embodiment shown in FIG. 6, when the pipe 162 is located at the mount position in a mount hole 14 of the cigarette lighter socket 12, a projection 22 of a first terminal 16 enters an annular groove 166, formed in the outer side surface of a heat conduction tube 66, to lock the pipe 162. At this time, a first electric contact 174 comes into contact with a projection 17 of the first terminal 16, and a second electric contact 176 comes into contact with a projection 24, constituted by a second terminal 18, while squeezing the projection 24.

When the pipe 162 is locked at the mount position in the mount hole 14, a cover 82 is pushed out by the wall surface of the casing, which surrounds the inlet port of the mount hole 14, against the biasing force of a coil spring 84 to a position where it covers a heat-insulating tube 67. Hence, a potential-restoration force for moving the pipe 162 from the mount position in the mount hole 14 to disconnect the first and second terminals 16 and 18 from the first and second electric contacts 174 and 176, respectively, is given to the pipe 162.

The operation of the flavor generation instrument shown in FIG. 6 will be summarized. First, in the state shown in FIG. 6, a heat reservoir 86 and a formed body 88 in the pipe 162 are heated by a coil heater 172. When the heater 172 maintains a predetermined temperature for a predetermined period of time, the projection 22 of the mount hole 14 is thermally deformed to be retreated. The pipe 162 is moved from the mount position by the action of the potential-restoration force of the coil spring 84 and projects from the mount hole 14. Subsequently, the pipe 162 is disconnected from the cigarette lighter socket 12, so that it can be subjected to inhalation of the flavor or simulated smoking.

The embodiment shown in FIG. 6 also may be altered such that the heater 172 is wound around the elongated heat reservoir 86 and that the formed body 88 of the material forms a hollow cylinder to surround the heater 172, as shown in FIG. 5.

The present invention has been described by way of its preferred embodiments shown in the accompanying drawings. The present invention can be practiced in various embodiments other than those shown in the drawings within the scope of the spirit of the invention.

What is claimed is:

1. A flavor generation device comprising:
   a casing having an air intake port for taking in air into said casing and a suction port through which a user inhales the flavor, and forming a gas flow path between said air intake port and said suction port;
   a flavor generation medium disposed in said casing to be exposed to said gas flow path and containing a flavor component, said flavor generation medium emitting said flavor component upon being heated; and
   a heat reservoir disposed in said casing to accumulate heat energy and heat said flavor generation medium with heat energy, wherein
   said casing has a heat conduction wall made of a heat-resistant heat-conductive material and is arranged to surround said heat reservoir, and a heat-insulating wall made of a heat-insulating material, said heat conduction wall being disposed between said air intake port and said heat insulating wall, and said heat insulating wall being disposed between said heat conduction wall and said suction port.

2. The flavor generation device according to claim 1, wherein said flavor generation medium comprises a formed body of a solid material containing said flavor component and is arranged adjacent to said heat reservoir.

3. The device according to claim 1, further comprising a heat-insulating cover slidably mounted on said casing to selectively cover said heat conduction wall.

4. The device according to claim 3, further comprising a spring configured to provide said cover with a biasing force toward a position at which said cover covers said heat conduction wall.

5. A flavor generation device comprising:
   (a) an external heating mechanism including
   an insertion hole for accepting and heating an elongated body, and
   a heater disposed along said insertion hole; and
   (b) a flavor generation article detachably inserted in said insertion hole of said external heating mechanism, said flavor generation article comprising
   an incombustible casing having an air intake port for taking in air into said casing and a suction port through which a user inhales the flavor, and forming a gas flow path between said air intake port and said suction port,
   a flavor generation medium disposed in said casing to be exposed to said gas flow path and containing a flavor component, said flavor generation medium emitting said flavor component upon being heated, and
   a heat reservoir disposed in said casing to accumulate heat energy and heat said flavor generation medium with the heat energy, said heat reservoir being arranged to receive the heat energy from said heater when said flavor generation article is inserted in said insertion hole of said external heating mechanism.

6. The flavor generation device according to claim 5, wherein said flavor generation medium comprises a formed body of a solid material containing said flavor component and is arranged adjacent to said heat reservoir.

7. The flavor generation device according to claim 5, wherein said heater comprises an electric heater.

8. The device according to claim 5, wherein said casing has a heat conduction wall made of a heat-resistant heat-conductive material and arranged to be heated by said heater of said external heating mechanism, and a heat-insulating wall made of a heat-insulating material, said heat conduction wall being arranged between said air intake port and said heat-insulating wall, and said heat-insulating wall being arranged between said heat conduction wall and said suction port.

9. The device according to claim 5, further comprising a mechanism configured to correlate an attaching/detaching operation of said flavor generation article in/from said insertion hole of said external heating mechanism and an on/off operation of said electric heater.

10. A flavor generation device comprising:
    (a) an external power supply mechanism including
    an insertion hole for accepting and heating an elongated body, and
    first and second terminals connected to a power supply and arranged in said insertion hole; and
    (b) a flavor generation article detachably inserted in said insertion hole of said external power supply mechanism, said flavor generation article comprising
    an incombustible casing having an air intake port for taking in air into said casing and a suction port through which a user inhales the flavor, and forming a gas flow path between said air intake port and said suction port,
    a flavor generation medium disposed in said casing to be exposed to said gas flow path and containing a flavor component, said flavor generation medium emitting said flavor component upon being heated,
    a heat reservoir disposed in said casing to accumulate heat energy and heat said flavor generation medium with the heat energy,
    an electric heater disposed in said casing to supply the heat energy to said heat reservoir, and
    first and second electric contacts exposed outside said casing and serving as circuit terminals of said electric heater, said first and second electric contacts coming into contact with said first and second terminals, respectively, when said flavor generation article is inserted in said insertion hole of said external heating mechanism.

11. The flavor generation device according to claim 10, wherein said flavor generation medium comprises a formed body of a solid material containing said flavor component and is arranged adjacent to said heat reservoir.

12. The device according to claim 11, wherein said formed body is arranged to be detachably disposed in said casing, and to surround said heat reservoir and said electric heater.

13. The device according to claim 12, wherein said heat reservoir comprises a hollow body in which said electric heater is disposed.

14. The device according to claim 12, wherein said electric heater comprises a coil heater which is wound around said heat reservoir.

15. A flavor generation device comprising:

a casing having an air intake port for taking air into said casing and a suction port through which a user inhales the flavor, and forming a gas flow path between said air intake port and said suction port;

a flavor generation medium disposed in said casing to be exposed to said gas flow path and containing a flavor component, said flavor generation medium emitting said flavor component upon being heated, said flavor generation medium including a formed body of a solid material containing said flavor component;

a heat reservoir disposed in said casing to accumulate heat energy and heat said flavor generation medium with heat energy; and an electric heater disposed in said casing to supply heat energy to said heat reservoir wherein said formed body is arranged adjacent to said heat reservoir to be detachably disposed in said casing, and to surround said heat reservoir and said electric heater.

16. The device according to claim 15, further comprising a power supply configured to sup-ply electrical energy to said electric heater.

17. The device according to claim 15, wherein said heat reservoir comprises a hollow body in which said electric heater is disposed.

18. The device according to claim 15, wherein said electric heater comprises a coil heater which is wound around said heat reservoir.

* * * * *